United States Patent
Tuunanen

(10) Patent No.: US 6,665,073 B2
(45) Date of Patent: Dec. 16, 2003

(54) ABSORBANCE MEASUREMENT

(75) Inventor: Jukka Tuunanen, Helsinki (FI)

(73) Assignee: Thermo Labsystems Oy, Helsinki (FI)

( * ) Notice: Subject to any disclaimer, the term of this patent is extended or adjusted under 35 U.S.C. 154(b) by 78 days.

(21) Appl. No.: 09/796,446

(22) Filed: Mar. 2, 2001

(65) Prior Publication Data

US 2001/0035956 A1 Nov. 1, 2001

(30) Foreign Application Priority Data

Mar. 3, 2000 (FI) .............................. 20000492

(51) Int. Cl.⁷ .............................................. G01N 21/78
(52) U.S. Cl. ...................................... 356/440; 356/436
(58) Field of Search ................................ 356/436, 437, 356/440, 246

(56) References Cited

U.S. PATENT DOCUMENTS

| | | |
|---|---|---|
| 3,164,663 A * | 1/1965 | Gale ........................ 356/436 |
| 4,260,252 A | 4/1981 | Wittenberg |
| 4,599,315 A | 7/1986 | Terasaki et al. |
| 4,762,798 A | 8/1988 | Deutsch |
| 5,795,748 A | 8/1998 | Cottingham |
| 5,963,318 A | 10/1999 | Held |
| 6,188,476 B1 * | 2/2001 | Hafeman et al. ........... 356/343 |

FOREIGN PATENT DOCUMENTS

| | | |
|---|---|---|
| DE | 40 16 619 A1 | 11/1991 |
| FI | 55093 | 1/1979 |
| GB | 1 486 210 | 9/1977 |
| JP | 60-222753 | 11/1985 |
| WO | WO 95/22406 | 8/1995 |

* cited by examiner

Primary Examiner—John R. Lee
Assistant Examiner—Anthony Quash
(74) Attorney, Agent, or Firm—Oblon, Spivak, McClelland, Maier & Neustadt, P.C.

(57) ABSTRACT

The invention relates to a method for measuring the absorbance of a sample. In accordance with the invention, an insert pervious to light is supported on a stand in the measuring well, the insert bottom being located below the sample surface. This allows the length of the light path in the liquid to be accurately selected.

17 Claims, 1 Drawing Sheet

ABSORBANCE MEASUREMENT

TECHNICAL FIELD

The invention relates to vertical measurement of light absorbance, comprising the absorbance measurement of a sample column of constant length. The invention is applicable especially when no reference sample is available or when a very exact measurement of the absorbance is required. The invention is applicable e.g. to determinations in clinical chemistry.

PRIOR ART

Under the Bouguer-Lambert Law, the absorbance of light passing through a sample is obtained with the formula $$a = e * c * d$$

in which
c is concentration
d is light path length and
e is constant.

In vertical measurement, the samples are usually located in wells that are open at their upper end. In that case, the height of the sample column is usually not known with sufficient accuracy. The curvature of the liquid surface also affects the determination of the exact height. This is no inconvenience if a reference sample with a known concentration is available. In fact, vertical measurement is then a preferable measuring method, because variations in the amount of diluting agent do not affect the measurement result.

In some applications, no reference sample is available. When a known substance is being measured, e is known. In order to obtain absolute concentration values, d must also be known with sufficient accuracy.

In horizontal measurement, the inner diameter of the cuvette determines the light path length d in the sample very accurately. This has been utilised also in some vertical photometers. They comprise a separate measurement duct, where absorbance is measured in a horizontal cuvette. This inherently results in a complex and expensive apparatus, since it requires measuring means both for horizontal measurement of ordinary wells, e.g., in a microtitration plate, and of a reference cuvette.

U.S. Pat. No. 5,963,318 discloses a vertical measuring cuvette having a lower measuring section and a neck part on the side of this. The cuvette is filled so that the liquid fills the measuring section to its total height, the free surface of the liquid being then on a higher level in the neck part. This allows vertical measurement at the measuring section through a liquid column with known height, e.g. a standard 10 mm liquid column. Such cuvettes can be measured in vertical photometry. However, the manufacture of such cuvettes is very troublesome; in practice they must actually be made by joining two pieces together. The manufacture of small cuvettes, e.g. having a diameter equalling the well in a microplate, is also troublesome. Thus, the cuvettes of the corresponding commercial application are relatively large-sized, and 8 such cuvettes can be placed in the rack of a 96-well microtitration plate.

GENERAL DESCRIPTION OF THE INVENTION

A method of absorbance measurement, an insert used in the measuring well and an absorbance measuring apparatus according to the independent claims have now been found. A number of embodiments of the invention are described in the dependent claims.

In accordance with the invention, the measuring well comprises an insert that is pervious to light and supported by a stand, placed with its bottom underneath the sample surface. In this manner, the distance between the insert bottom and the measuring well bottom will remain constant in all cases, and the absorbance of a sample column with constant height can be determined. The sample surface may surround the insert bottom. The insert bottom may be a horizontal plane. The insert also has an upper surface. This may also be a horizontal plane. The invention also relates to a measuring well comprising an insert. The invention also relates to a method for measuring the absorbance of a sample with constant thickness.

In this method, the measuring light can be conducted from the top to the bottom or from the bottom to the top through the sample. Any disturbing air bubbles remaining between the insert bottom and the liquid sample may be removed e.g. by shaking before the measurement. The bottom may also be designed such that the bubbles are transferred beyond the area of measurement. The invention also relates to a measuring apparatus for determining absorbance through an insert.

The insert itself may be a well-like body. It may also be a closed body defined by the bottom and the upper surface.

The insert may be a body detached from the measuring well, and in that case it is placed into the well only when necessary. This allows the well to be used for conventional measurement if desired. In addition, the same insert can also be used in different wells, especially in wells with varied height. In connection with a detached insert, a special tool can be used to grip the insert. This tool is preferably such that grips the insert outside of the surfaces intended for conducting the measurement light. In this way the surfaces pervious to light in the measurement will remain as intact and clean as possible. The invention also relates to a tool for handling the insert.

The insert stand is supported by the well bottom, and thus the insert will be automatically positioned always at the same distance from the well bottom. The stand may also comprise centering means for centering the insert in the well. This allows light to be conducted from the same point both at the center of the well and of the insert in each case. The centering means may comprise one or more, e.g. three projections matching the well wall. The stand may have legs, which also act as centering means. In that case, they preferably act as springs and protrude by pressing against the well wall. The insert or the stand may also comprise centering means separate from the legs, e.g. lateral drags matching the well wall. This allows the legs to be supported by the bottom aloof from the corner between the wall and the bottom, because this angular shape may cause inaccuracies. This avoids the use of legs acting as springs, and consequently any distance errors caused by them. The separate centering means may have very high elasticity so that the same insert is usable in wells with markedly different widths.

At the upper end of the insert, a cover may be provided to close the well when the insert is in position in the well. The cover protects the sample and also prevents evaporation.

The measurements are usually performed on plates, each of which comprises several measuring wells. The most commonly used plate is the one called microtitration plate, which has 8*12 wells with a 9 mm distribution. If necessary, an inner well can be placed in one or more wells on the plate. The invention also relates to a plate having an insert in one or more of its wells. There may be individual inserts or several inserts combined to form strips or matrices, which are suitable for use on a plate with many wells.

The insert stand may have one or more legs. A separate insert may have such legs that press against the inner walls of the measuring well. In this manner, the insert will remain in position as well as possible. There may be e.g. 3 . . . 5, preferably 3 legs.

At the outer edge of the bottom of a stand supported on the bottom of the inner well, a deflecting means may be provided to avoid rounding of the well bottom angle. The deflecting means may be e.g. a rounding or a bevel. Owing to the deflecting means, the stand will always reach the bottom reliably.

The insert stand may be an integrated part of the insert. It may also be separately from the actual insert. In that case, it forms a base on which the actual insert is placed.

In accordance with the invention, the height of the absorbance is measured through a liquid column whose height is exactly known. The accuracy required in practical operation is of the order of 1%, which is easily achieved with the invention. Nevertheless, the measuring well can be made in the usual size. Any supplementary parts for normal use can be made by means of ordinary techniques of plastics commonly used in the field.

DESCRIPTION OF THE DRAWINGS

The accompanying schematic drawings pertain to the following detailed description of some embodiments. In the drawings

DETAILED DESCRIPTION OF SOME EMBODIMENTS OF THE INVENTION

Figure 1:
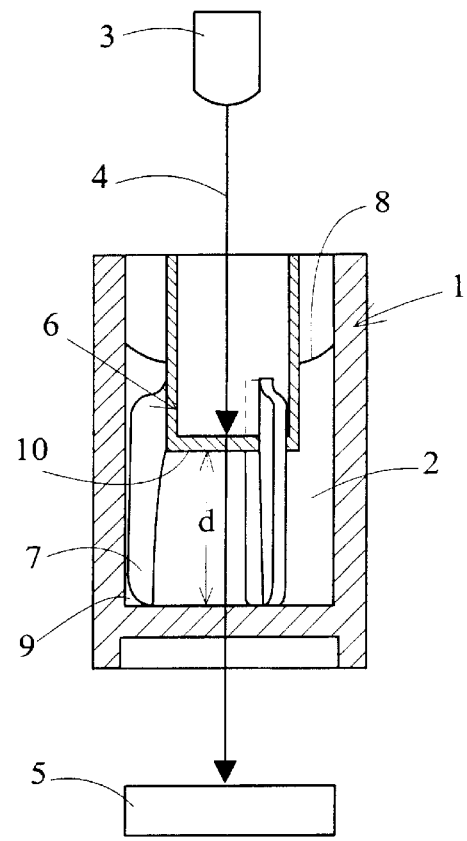
FIG. 1 shows a measuring well and an insert placed in this.

The apparatus of FIG. 1 comprises a measuring well 1 for vertical photometry. Dosed in the well there is a liquid sample 2, whose absorbance is measured by conducting a bundle of light beams 4 from a light source 3 above to a detector 5 below. Placed in the well there is an inner well 6 standing on the well bottom supported by legs 7. The minimum volume of the sample and the height of the legs of the inner well have been dimensioned so that the sample surface 8 will be located above the bottom of the inner well fitted into position. Thus the distance d over which the light beam bundle passes through the sample is always exactly determined regardless of the sample volume, provided that it is great enough for the sample surface to be located above the inner well bottom. The curvature or vibration of the liquid surface do not either interfere with the measurement. A plurality of measuring wells have usually been combined to form a plate comprising several wells.

The inner well 6 can be made of suitable plastic by conventional methods (e.g. injection moulding) so as to achieve adequate dimensional precision (e.g. about 0.01 mm). A suitable sample column to be measured may have a height of e.g. 5.00 mm. An inner well made of plastic is inexpensive, and can thus be disposable along with the plate. Owing to the well-like shape, the material requirement is minimised.

In the present case the inner well 6 has three legs 7, but there may be more, e.g. 4 or 5. When free, the lower end of the legs extend slightly broader than the bottom of the well 1. However, the legs yield sufficiently for the inner well to be fitted into position, with the legs pressing against the inner walls of the well. The inner well remains tightly in position owing to friction.

The lower corners 9 of the legs 7 of the inner well 6 are rounded at their outer edge. Owing to this, the rounded edge of the measuring well bottom will not hamper tight fitting of the inner well.

The legs 7 are preferably attached to the inner well 6 by soft joining interfaces in order to achieve a strong, but still thin construction.

The inner well 6 usually has a planar bottom 10. If desired, it may, however, be shaped as a suitably curved lens. In some special cases, a lens might be a benefit in the measurement.

Any bubbles formed between the inner well bottom and the sample and interfering with the measurement can be removed e.g. by suitably shaking the measuring well and the inner well. To promote bubble removal, the bottom can be made slightly sloping (or conical). A concave lens bottom also contributes to bubble removal.

The inner well 6 can be positioned in one or more wells 1 in the plate to be used.

Figure 2:
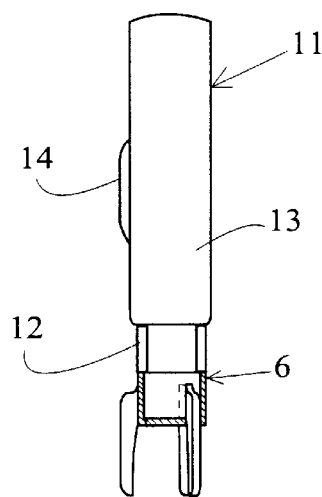
FIG. 2 shows a tool for shifting the insert and FIG. 3 shows a second insert.

The inner well 6 is preferably fitted into position by means of a special tool. The tool 11 illustrated in FIG. 2 has a tip cylinder 12 engaging the mouth of the inner well 6 by friction. The tip cylinder moves within the outer cylinder 13, whose lower edge matches the upper edge of the inner well. The inner cylinder can be shifted within the outer cylinder with the aid of a pusher 14 provided outside the outer cylinder mantle. The inner well is gripped by pushing the inner cylinder of the tool in lower position into its mouth. When the inner cylinder is lifted within the outer cylinder, the lower edge of the outer cylinder detaches the inner well from the inner cylinder by pressing. Another optional tool is such that has claws that are provided at the lower end of the outer cylinder and grip the outer surface of the upper end of the inner well, the inner well being released by pressing the inner cylinder down.

Figure 3:
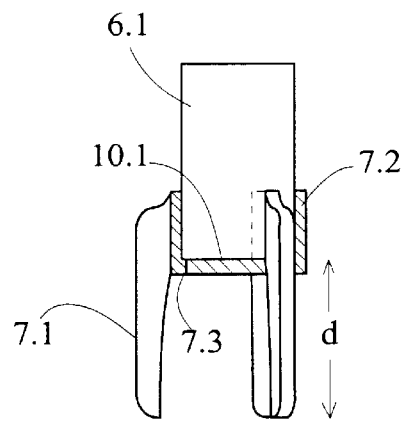

When measurement is required on short wavelengths (e.g. 200 . . . 340 nm), plastic materials are usually no longer usable. Then silica is usually used as the material. FIG. 3 illustrates an insert used in such a case.

The insert 6.1 of FIG. 3 is a closed cylinder. It is fitted on a tripod formed by legs 7.1. The legs are joined by a ring 7.2 which matches the diameter of the inner well and has at its lower end an inwards support ring 7.3, on which the inner well is supported.

The inner well 6.1 can be made of any adequate material suitable for short wavelengths, such as silica, by cutting suitable lengths of a bar. The tripod may be made of a suitable less expensive plastic. A tool equipped with outer grip claws can be used for handling the inner wells.

For economical reasons, the insert 6.1 may be used several times. The tripod may then be disposable, so that it is easy to wash only the insert without inner corners between measurements. However, the tripod may also be an integrated part of the insert.

What is claimed is:

1. A method for measuring the absorbance of a sample by conducting light through the sample, in which method the sample is dosed in a well having a bottom pervious to light, and the light is passed vertically through the sample, characterized in that before introducing light into the well, an insert with a supporting stand, which insert is pervious to the light and has a closed bottom and a wall with an upper edge around the bottom, is placed in the well such that the sample surface is located above the bottom but below the upper edge of the wall.

2. A method as defined in claim 1, in which an insert detached from the well is placed in the well.

3. An insert to be placed within a sample well for measuring absorbance, characterized in that the insert has a stand, and supported by the stand, the insert can be placed on the bottom of a measuring well containing sample, through which measuring light is passed in the vertical direction, that the insert is pervious to the light and that it includes an inner well having a continuous surface that comprises a bottom, which is located below the surface of the sample, and a wall that surrounds the bottom and has an upper edge located above the surface of the sample.

4. An insert as defined in claim 3, in which the insert has an upper surface which together with the bottom and the wall of the insert defines a closed space.

5. An insert as defined in claim 3, in which the stand is integrated with the insert.

6. An insert as defined in claim 3, in which the stand of the insert is detachable from the insert.

7. An insert as defined in claim 3, in which the insert is a body separate from the measuring well and in which the stand of the insert placed in the well has legs which press against the inner wall of the measuring well.

8. An insert as defined in claim 3, in which the insert is a body separate from the measuring well and to be used together with a tool for handling the insert.

9. An apparatus for measuring the absorbance of a sample, comprising a measuring well in which the sample to be measured is placed, a light source for passing measuring light vertically through the well and the sample contained in the well, and a detector for receiving the light that has been passed through characterized in that the measuring well comprises an insert as defined in any of claims 3 and 4 through 8.

10. An insert as defined in claim 3, wherein the bottom and the wall of the insert form an inner wall.

11. A method for measuring absorbance of a sample, said method comprising the step of:

providing the sample in a well having a bottom surface pervious to light;

providing within the well an insert that is pervious to light, the insert having a closed bottom and wall extending around the bottom with an upper edge, the insert having a supporting stand that supports the insert on the bottom surface of the well wherein a surface of the sample in the well is located above the bottom of the insert and below the upper edge of the insert;

conducting light through the insert, the sample, and the bottom surface of the well; and measuring the absorbance of the sample based upon the conducted light.

12. An insert as defined in claim 11, wherein said insert body has an upper surface, and wherein said upper surface, said wall and said bottom of said insert body define a closed space.

13. An insert as defined in claim 11, wherein said supporting stand is integrated with said insert body.

14. An insert as defined in claim 11, wherein said supporting stand is detachable from said insert body.

15 An insert used during measurment of absorbance of a sample within a well, said insert comprising:

an insert body that is pervious to light, said insert body having a closed bottom and a wall extending around said bottom with an upper edge;

a supporting stand attached to said insert body and adapted to support said insert body on a bottom surface of the well whereby a surface of the sample in the well is located above said bottom of said insert body and below said upper edge of said insert body.

16. An insert as defined in claim 15 wherein said bottom of said insert body and said wall of said insert body form an inner well.

17. An apparatus for measuring absorbance of a sample, said apparatus comprising:

a well adapted to receive the sample, said well having a bottom surface;

an insert including an insert body that is pervious to light, said insert body having a closed bottom and a wall extending around said bottom with an upper edge, said insert further including a supporting stand attached to said insert body, said supporting stand supporting said insert body on said bottom surface of said well whereby a surface of the sample in said well is locate above said bottom of said insert body and below said upper edge of said insert body;

a light source configured to conduct measuring light through said insert body, the sample, and said bottom surface of said well; and a detector configured to receive the conducted measuring light.

* * * * *